United States Patent [19]
Shepich

[11] Patent Number: 5,603,336
[45] Date of Patent: Feb. 18, 1997

[54] BED FOOTBOX FOR MEDICAL PATIENT'S

[76] Inventor: Frank G. Shepich, 2627 Dryden Rd., El Cajon, Calif. 92020

[21] Appl. No.: 526,824

[22] Filed: Sep. 11, 1995

[51] Int. Cl.⁶ .............................. A61F 5/37; A47C 20/02
[52] U.S. Cl. .................................................. 128/882; 5/650
[58] Field of Search .................................... 128/845, 882, 128/846; 602/28, 15, 23; 5/505.1, 630, 636, 648–651

[56] References Cited

U.S. PATENT DOCUMENTS

| | | | |
|---|---|---|---|
| 2,911,657 | 11/1959 | Streeter | 5/651 |
| 3,345,654 | 10/1967 | Noble | 5/505.1 |
| 3,532,336 | 10/1970 | Baker | 5/650 |
| 5,101,526 | 4/1992 | Smith | 5/651 |

*Primary Examiner*—Michael A. Brown
*Attorney, Agent, or Firm*—Charles C. Logan, II

[57] ABSTRACT

A footbox for medical patient's that is placed at the foot of their bed. It has a horizontal base having a rear wall extending up from its rear end. Two pairs of laterally spaced walls form a left foot receptacle and a right foot receptacle and they extend from the rear wall. The three walls forming each of the respective foot receptacles have foam pads lining their inner surfaces to provide cushioning for the patient's feet. A cushioned pad extends across the width of the base in front of the respective left and right foot receptacles and is of such a height that the patient's heel will not contact the top surface of the base inside the respective foot receptacle.

10 Claims, 2 Drawing Sheets

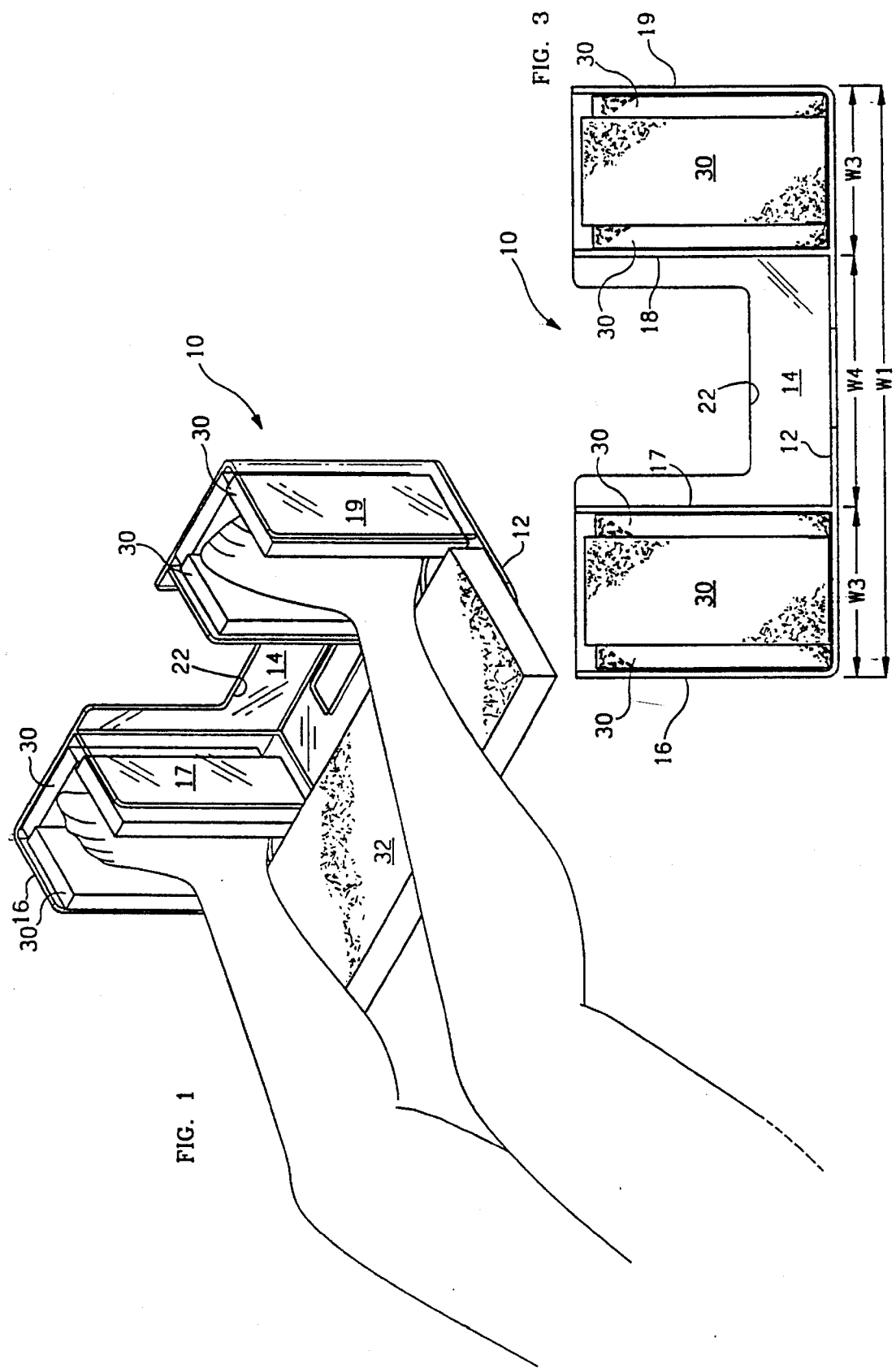

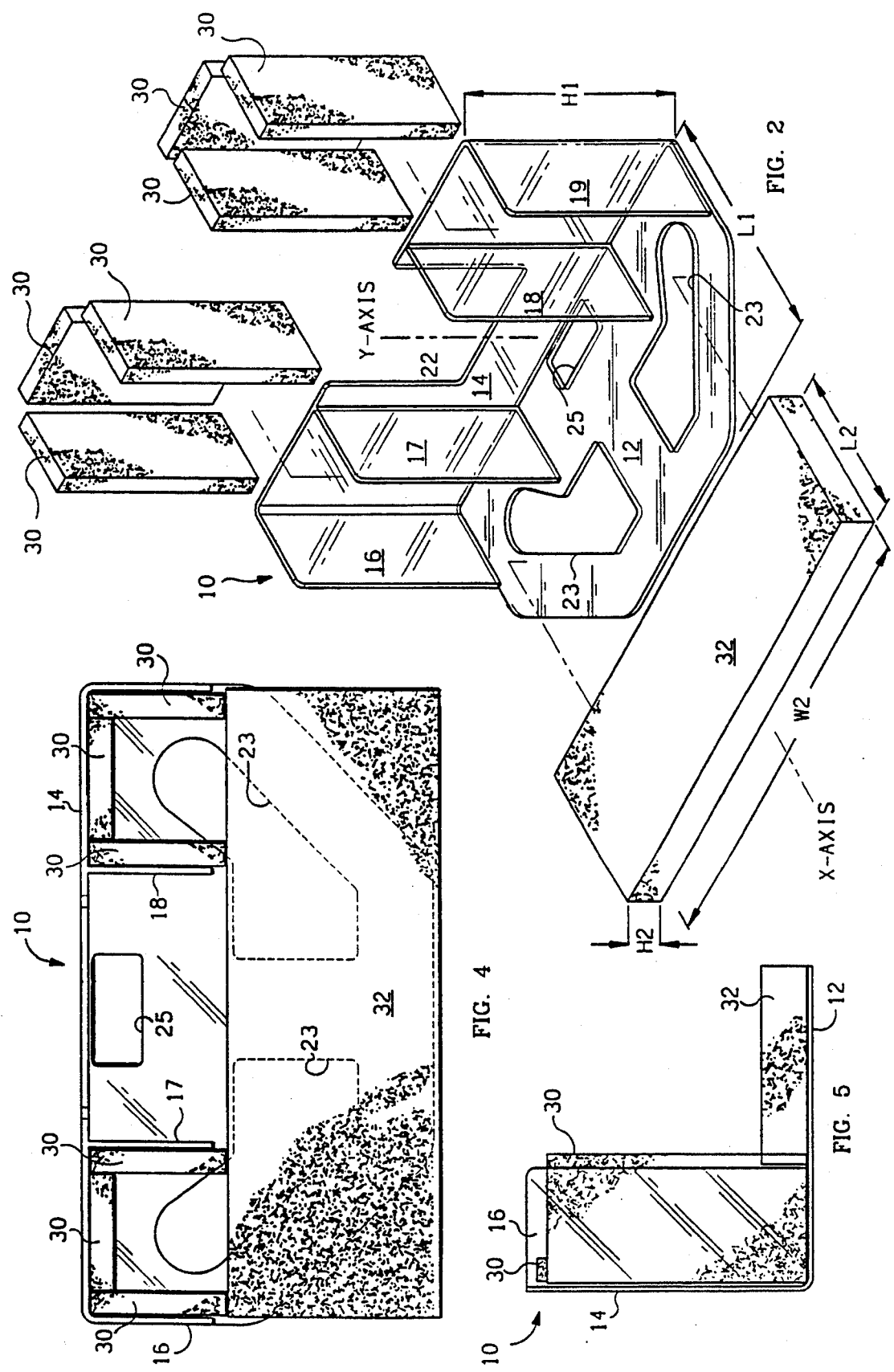

BED FOOTBOX FOR MEDICAL PATIENT'S

BACKGROUND OF THE INVENTION

The invention relates to a medical device and more specifically to one for properly supporting the feet of a patient while they are in bed.

People that are bed ridden often develop or have drop foot or sway foot. These patient's therefore require some type of device or structure to properly support their feet while they are bed ridden. People who are bed ridden often have pain from the bed sheets and blankets pressing on/or touching the top of their toes. People having crippling diseases such as Multiple Sclerosis or other diseases may require that their legs be supported and spaced from each other in order to prevent pain and discomfort.

It is an object of the invention to provide a novel bed footbox that can be used by bed ridden patients to keep the sheets and blankets from pressing down on the tops of their feet.

It is also an object of the invention to provide a novel bed footbox that will keep a bedridden person's feet properly separated from each other.

It is another object of the invention to provide a novel bed footbox that can be used by bed ridden patients to prevent or alleviate the discomfort of drop foot and sway foot.

It is another object of the invention to provide a novel bed footbox that is economical to manufacture and market.

It is a further object of the invention to provide a novel bed footbox that is lightweight and can be easily carried.

It is an additional object of the invention to provide a novel bed footbox that eliminates pressure on the heels of the feet of the bedridden patient.

SUMMARY OF THE INVENTION

The novel bed footbox has been manufactured from lightweight plastic material and foam padding. The bed footbox is compact and easily stored when not in use. It can be easily carried by a handgrip cutout in the base of the device.

The bed footbox in use is placed at the foot of a patient's bed. The patient's feet are then positioned in the respective left and right foot receptacles. Due to the height of the base foam pad, their calves or the back of their ankles will rest on the base foam pad and the bottom and heels of their feet will not rest on the top surface of the base plate. Instead they will be confined to the heel receptacle recess formed at the bottom of each of the respective left and right foot receptacles this allows better air circulation around the entire foot.

The foam pads that are inserted into the respective foot receptacles provide both lateral cushioning and also support for the bottom of the patient's foot which prevents or minimizes drop foot. The height of the top edges of the respective foot receptacles is spaced above the toes of the patient so that the weight of the sheets or blankets do not press down upon the patient's toes and give them discomfort such as has occurred in the past.

The bed footbox is made of materials that allow it to be easily cleaned and disinfected between use by different patients. The bed footbox is easy to use and can be installed or positioned on the patient's bed by non medical personnel. It can be used in a medical facility or at home.

The handgrip cutout makes the bed footbox easy to carry. The lightweight materials also make it light to carry. There are no straps holding the patient's legs or feet and this reduces patient anxiety.

DESCRIPTION OF THE DRAWINGS

FIG. 1 is a front perspective view of the novel bed footbox for medical patient's showing a person's feet inserted therein;

FIG. 2 is an exploded front perspective view of the novel bed footbox for medical patients;

FIG. 3 is a front elevation view of the novel medical bed footbox for medical patients;

FIG. 4 is a top plan view of the novel bed footbox for medical patients; and

FIG. 5 is a side elevation view of the novel bed footbox for medical patients.

DESCRIPTION OF THE PREFERRED EMBODIMENT

The novel bed footbox for medical patient's will now be described by referring to FIGS. 1–5 of the drawings. The bed footbox is generally designated numeral 10.

Bed footbox 10 has a width W1 and a length L1. W1 is in the range of 12–26 inches. L1 is in the range of 8–18 inches. Rear wall 14 extends upwardly at a 90 degree angle from the rear edge of base 12. Rear wall has a height H1 in the range of 8–20 inches. Left outside upright wall 16 and left inside upright wall 17 are substantially vertical and extend from rear wall 14 to form a left foot receptacle. Right inside upright wall 18 and right outside upright wall 19 also extends from rear wall 14 and they form a right foot receptacle. The left and right foot receptacles have a width W3 that is in the range of 4–8 inches and a height H1 that is in the range of 8–20 inches. The two foot receptacles are spaced apart a distance W4 that is in the range of 6–18 inches.

In the embodiment illustrated, base 12, rear wall 14 and upright walls 16–19 are made of clear acrylic plastic. Upright walls 16 and 19 are integrally formed from rear wall 14. The respective components are connected together by common state of the art adhesives. Base 12 has a longitudinal x-axis and rear wall 14 has a vertical y-axis. Cutouts 22 and 23 are formed in base 12 for the purpose of saving material and lightening its weight. Handgrip cutout 25 makes the unit easy to carry with a single hand. Rear wall cutout 22 makes it easier to access handgrip cutout 25 and also lightens the weight of the unit.

Foot pads 30 are inserted into the respective left and right foot receptacles and provide cushioning for the patient's feet against the surrounding walls. Base foam pad 32 has a width W2 in the range of 12–26 inches and a length L2 in the range of 4–14 inches. It also has a height H2 in the range of ½–2 inches. Placed on base 12 with its edges abutting the front edges of the respective left and right foot receptacles, base foam pad 32 elevates the heel of the person's foot in the respective foot receptacles to form heel recesses so that they do not touch the top surface of base 12.

What is claimed is:

1. A bed footbox for medical patient's comprising:

a horizontally oriented base having a top surface, a bottom surface, a front edge, a rear edge, a left edge, a right edge, a longitudinal x-axis, a width W1 and a length L1;

an upright oriented rigid rear wall having a top edge, a bottom edge, a left edge, a right edge, an upright y-axis, a front surface and a rear surface; the bottom edge of said rear wall being rigidly connected to the top surface of said base and it extends laterally across the width of said base;

a first pair of laterally spaced upright walls each having an inner surface, a top edge, a bottom edge, a front edge, a rear edge; said rear edges being secured to the front surface of said rear wall to form a left foot receptacle; said upright walls being spaced apart a preselected distance W3; the bottom edges of said upright walls being rigidly connected to the top surface of said base;

a second pair of laterally spaced upright walls each having an inner surface, a top edge, a bottom edge, a front edge and a rear edge; said rear edges being secured to the front surface of said rear wall to form a right foot receptacle, said upright walls being spaced apart a preselected distance W3; the bottom edges of said upright walls being rigidly connected to the top surface of said base;

said left foot receptacle and said right foot receptacle being spaced apart a preselected distance W4;

means for cushioning the inner upright wall surfaces of said left and right foot receptacles; and cushioning means on the top surface of said base and it extends across the front ends of said respective left and right foot receptacles; it has a preselected height H2 that prevents a person's heel from contacting the top surface of said base when their feet are inserted into said left and right foot receptacles.

2. A bed footbox for medical patient's as recited in claim 1 wherein said base, rear wall and first and second pairs of laterally spaced upright walls are all made of plastic material.

3. A bed footbox for medical patient's as recited in claim 1 wherein W1 is greater than L1.

4. A bed footbox for medical patient's as recited in claim 1 further comprising a handgrip cutout in said base adjacent its rear end and positioned between said left and right foot receptacles.

5. A bed footbox for medical patient's as recited in claim 1 further comprising a rear wall cutout extending down from the top edge of said rear wall and being positioned between said left and right foot receptacles.

6. A bed footbox for medical patient's as recited in claim 1 wherein H1 is in the range of 8–20 inches.

7. A bed footbox for medical patient's as recited in claim 1 wherein W3 is in the range of 4–8 inches.

8. A bed footbox for medical patient's as recited in claim 1 wherein W2 is in the range of 12–26 inches.

9. A bed footbox for medical patient's as recited in claim 1 wherein L1 is in the range of 8–18 inches.

10. A bed footbox for medical patient's as recited in claim 1 wherein H2 is in the range of ½–2 inches.

* * * * *